United States Patent
Drake et al.

(10) Patent No.: US 6,992,233 B2
(45) Date of Patent: Jan. 31, 2006

(54) MATERIAL DELIVERY SYSTEM

(75) Inventors: James Franklin Drake, Minneapolis, MN (US); Mark Harold Ereth, Rochester, MN (US); Lynn R. Skow, North Branch, MN (US)

(73) Assignee: MedaFor, Inc., Minneapolis, MN (US)

( * ) Notice: Subject to any disclaimer, the term of this patent is extended or adjusted under 35 U.S.C. 154(b) by 294 days.

(21) Appl. No.: 10/164,365

(22) Filed: May 31, 2002

(65) Prior Publication Data

US 2003/0225354 A1  Dec. 4, 2003

(51) Int. Cl.
 *A61F 13/00* (2006.01)

(52) U.S. Cl. .................. 602/48; 424/443; 424/446; 424/447; 424/448; 424/449; 604/304; 604/307

(58) Field of Classification Search .......... 604/304, 604/307, 43–59, 309, 306; 424/447, 448–449, 424/443, 446; 602/48, 41–42
See application file for complete search history.

(56) References Cited

U.S. PATENT DOCUMENTS

| | | | |
|---|---|---|---|
| 4,373,519 A | 2/1983 | Errede et al. | 128/156 |
| 4,808,172 A * | 2/1989 | Murata | 604/306 |
| 4,858,604 A | 8/1989 | Konishi | 128/156 |
| 5,004,610 A | 4/1991 | Osborne et al. | 424/448 |
| 5,851,549 A | 12/1998 | Svec | 424/448 |
| 6,060,461 A * | 5/2000 | Drake | 514/54 |
| 6,241,697 B1 | 6/2001 | Augustine | 602/2 |
| 6,350,339 B1 | 2/2002 | Sessions | 156/250 |

FOREIGN PATENT DOCUMENTS

| | | |
|---|---|---|
| WO | WO 00/27327 | 5/2000 |
| WO | WO 01/12116 A1 | 2/2001 |
| WO | WO 01/64148 A1 | 7/2001 |

* cited by examiner

*Primary Examiner*—Kim M. Lewis
(74) *Attorney, Agent, or Firm*—Mark A. Litman & Associates, P.A.

(57) ABSTRACT

A delivery system for the delivery of flowable medicinal, therapeutic or medicine materials has a strip with flowable material contained and restrained therein. A removable seal is provided, so that when the removable seal is removed, the flowable material will flow from a storage area onto a site selected for treatment. The removable seal may be provided with additional features such as absorbent coatings, or additional disinfectants coatings useful in preparing the wound surface to receive the flowable wound treatment material. A preferred composition is a system, article and method for the enhancement of clotting in wounds with extravascular blood flow, especially where the surface of the tissue has been broken.

29 Claims, 3 Drawing Sheets

MATERIAL DELIVERY SYSTEM

BACKGROUND OF THE INVENTION

1. Field of the Invention

The present invention relates to the field of topical application of medicinal or therapeutic material to tissue particularly for the reduction of bleeding, especially for enhancing the formation of clots on the surface of wounds and/or providing specific targeted therapy to a wound site. Devices for applying such medicinal materials are described.

2. Background of the Art

External wounds and concomitant bleeding are the most common injuries suffered by animals. Scratches, cuts, abrasions, lacerations, punctures and other categories of damage to layers of tissue, especially skin, each act to breach the protective tissue and blood vessels, allowing blood to flow out of its normal passageways. Bleeding provides a first line defense against damage from the ancillary effects of the trauma that caused the injury. The flow of blood washes material out of the wound and the blood clots to seal the wound area. The types of materials washed from the wound by the flow of blood from the traumatized area includes material introduced into the wound area by any foreign object which caused the wound (including biological species such as bacteria and viruses and inorganic species such as particulates). The clotting prevents migration of materials into the wound area, and therefore into the animals body, thus reducing the likelihood of subsequent infection of the wound, even after materials originally introduced into the wound have been removed or reduced in volume by the initial blood flow.

Clotting is essential to both the short term and long term process of healing the wound. In the short term, after the wound has been partially cleansed by blood flow, the clotting entraps these removed materials so that they will not easily reenter the wound and stops the blood flow so that excessive blood loss will not occur. In the long term, the clot secures the wound minimizing additional tissue trauma (e.g., from flexing of the area) and preventing additional contaminants from entering the wound and blood stream.

Clotting is a complex biological process, driven by a series of cascading organic/biological chemical reactions which must occur in a specific sequence to cause the final effect of protecting the wound. In lay terms, the events in a simple wound where blood flow has occurred can be described as following a reaction path where a) Blood cells leak into a wound area;
b) Blood vessels usually contract in the wound area to reduce the flow of blood;
c) Platelets in the blood aggregate and adhere to tissue at the damaged site, even plugging small blood vessels;
d) Platelets also interact with collagen, phospholipids, and tissue factor (a lipid-containing protein or lipoprotein, that stimulates blood clot formation);
e) The platelets break-up and release thromboplastin, a poorly defined mixture of phospholipids and proteins that activate a series or cascade of reactions, usually catalyzed by serine proteases. The final product of these reactions is the enzyme thrombin which catalyses the conversion of the soluble blood protein, fibrinogen, to insoluble fibrin;
f) The platelets provide nuclei upon which fibrin is bound to form the first stage of the moist clot, followed by subsequent maturation of the clot to form a firm coherent mass;
g) Tissue forming cells, fibroblasts, approach the wound and associate with the moist clot to strengthen the region;
h) The clot contracts and dehydrates, usually through evaporative processes, although there may be some absorption of liquid into the tissue;
i) Phagocytes (white blood cells) move into the wound area to ingest microorganisms, cellular debris and any residual foreign matter;
j) Epidermal cells at the edge of the wound divide and build a bridge across the wound.

The actual chemical and biological processes involved in the clotting process are quite complex and sophisticated. The process must be very selective, forming clots under only exacting conditions, so that clot formation does not occur in the circulatory system where clotting would itself be dangerous, causing phlebitis and certain types of strokes.

Wound management and clotting enhancement for wounds has taken many different paths over the years. There are a wide variety of different methodologies available for the management of wounds, depending, at least in part upon the type of wound and its severity. The two most common and effective treatments for minor bleeding wound management, following cleansing of the wound area, include direct application of pressure to the wound area and the topical application of an absorptive bandage to the wound surface. To assure the reduction of direct or secondary infections, all wound management should include cleansing and application of an antimicrobial agent to the wound area. After this cleansing step, the other methods may follow to control bleeding and prevent contamination of the wound. Direct application of pressure is usually effected by application of pressure manually or with a light wrapping. A sterile article is placed over the wound and pressure applied to the wound through the sterile article (e.g., a fabric, such as gauze, cotton ball, bandage, or other available, preferably sterilized or at least cleaned fabric). The pressure acts to assist in closing blood vessels in the area to reduce blood flow, absorb some of the initial blood flow with the highest content of foreign matter carried therein, and to stabilize the movement of the blood so that clotting is given time to initiate. The application of bandages to the wound area primarily acts to absorb excess blood, flow, provide a longer term barrier over the wound against introduction of foreign agents, protect the clot while it is still fragile (allowing it to dehydrate in the first twenty-four hours), and possibly carry and retain antimicrobial material to the wound surface.

The use of lasers, alone or in combination with topically applied patch materials (e.g., an elastin patch made from animal tissue), has been suggested for field treatment of bleeding wounds, both internal wounds and external or topical wounds. This has been specifically suggested as a field treatment, especially for the military, police, fire, and rescue services. Lasers by themselves can cauterize and seal vessel and organ wounds, and the patch can provide additional structural support for the area. ttp://detnews.com/96/discover/9701/05/12300058.htm.

Many folk remedies have also been applied as abrasion, but not open wound, treatments. For example, www://.drchristopher.com/ail/abrasio3.htm suggests the use of specific natural material treatments for abrasions where the skin has not been broken. The natural herbal agents include wheat grass chlorophyll, comfrey, healing ointment (comfrey, marshmallow, marigold, beeswax and oils), myrrh, plantain (and banana is also well known), and cayenne pepper. These materials may be applied directly to the abrasion area or carried on another surface, often with wetting suggested to retain the herbal abrasion treatment material. An Asian home remedy includes Dit Da Jao ("Iron Wine) which is a tincture remedy applied to relieve pain, stimulate blood flow and chi flow, and break up clots and bruises. The tincture is made up from powdered herbs and alcohol, with strained herbal residue discarded and the liquid tincture applied to the wound surface. The herbs to be used include Arnica blossom, comfrey, blessed thistle, goldenseal root, ginger root, Myrrh, sasparilla root, and witch hazel. Http://ww.aikidofaq.com/n.sub.—section51.html)

Newer technology for wound management is the use of chemical bandages, or literally polymeric film-forming material over the wound area. This technology has passed from a fairly unsophisticated application of liquid glues (e.g., cyanoacrylate adhesives, gelatinous glues, and UV curable polymers) to the wound surface. In 1998, only the second liquid glue was granted FDA approval for use as stitches in addition to clotting enhancement, the glue apparently comprising a formaldehyde content cyanoacrylate. This glue is Closure Medical Corporation's DermaBond™, which is used as an alternative to Baxter HealthCare Corporation's Tisseel™, which is made from two blood proteins that naturally cause blood to clot. The cyanoacrylate must have a strong tendency for tissue irritation and carries a standard recommendation against use with patients with sensitivities to acrylates and formaldehyde, which are fairly common. HealthCare Corporation's Tisseel™, which is made from specific blood proteins thrombin and fibrinogen, is relatively expensive to manufacture. In addition, the use of human or animal derived protein compositions carries the risk of contamination by infectious agents such as hepatitus viruses, Human Immuno-Deficiency (HIV) viruses, or prions such as have been related to mad cow disease (bovine spongiform encephalitis) and Creutzfeld-Jakob disease. The Cryoseal™ clotting system uses cryoprecititated proteins obtained from the patients blood as an adhesive. This fibrin glue adhesive is prepared and applied using a floor-standing, air-driven device in an operating theater.

U.S. Pat. No. 6,060,461 describes a method for enhancing the formation of clots on a wound of an animal where blood is present comprising the steps of applying porous particles with dimensions of from about 0.5 to 1000 micrometers to at least a portion of said wound where blood is present in said wound, allowing said porous particles to remain in contact with said blood in said wound while clotting initiates in said wound. The porous particles may have molecular sieve cutoff values between about 5,000 Daltons and 200,000 Daltons. The pores may comprise from 5 to 75% by volume of the porous particles.

PCT Application Publication WO 00/27327 describes a novel hemostatic composition comprising a substance containing uncharged organic hydroxyl groups and a substance containing at least one of a halogen atom and an epoxy group, which composition induces rapid blood coagulation and hemostasis at a wound or bleeding site. Examples of methods of application of the composition include, but are not limited to bags of materials, patches and bandaid-type patches, segments to be packed into cavities, fibers, fabrics, and the like.

It is known that fibrin clots are formed in vivo based upon the reaction of fibrinogen and thrombin in the presence of calcium ions. The initial phase of wound healing starts after the formation of fibrin clot, and involves the mobilization of cells from surrounding undamaged tissue. Normally, the earliest cells mobilized to the wound are inflammatory where they are active for a period of at least 1–3 days following injury. Subsequently, they are displaced by cells of the mesenchyme lineage which are immobilized into, navigate through and digest fibrin and replace fibrin with extracellular matrix (ECM) of different collagen types, fibronectin and hyaloron. Endothelial cells also infiltrate the fibrin and generate microcapillary structures. Ultimately, these cells replace the provisional fibrin matrix with granulation tissue populated by parenchymal cells and vasculature in secreted ECM.

Human fibroblasts are the major cellular entities responsible for the regeneration of the extracellular matrix (ECM) within the wound bed. Human fibroblasts also express specific membrane receptors to fibrinogen and thrombin. In the case of skin wounds, human fibroblasts reform the matrix of the dermis. For example, during the course of healing of an incisional skin wound, human fibroblasts are mobilized from the surrounding tissue and enter into the fibrin clot, help dissolve it and generate as well as reform the collagens (i.e. type I and type III) in the extracellular matrix. Based upon these properties of human fibroblasts, fibroblast implants have been suggested as a means for supplementing the body's natural wound healing regime (Gorodetsky, R., et al. Radiat. Res. 125:181–186 (1991)).

Benzoylated hyaluronic acid (HA) sheets containing holes or pores have been used as a carrier for fibroblasts and keratinocytes for wound healing (Andreassi, L., et al. Wounds 3(3): 116–126 (1991)). Specifically, HA sheets are cultured with these cells and then affixed to the site of the burn injury, where the cells migrate out of the sheet and accelerate the rate of wound regranulation. A major problem with implanted HA sheets, however, is that they are not metabolized by tissue, are cumbersome to administer, and may result in long-term immunological problems.

Purified fibrin(ogen) (which is known in the art as a mixture of fibrin and fibrinogen) and several of its lytic fragments (i.e. FPA, FPB, D and E) have been shown to be chemotactic to a variety of cells including macrophages, human fibroblasts (HF) and endothelial cells (Gorodetsky, R., et al. J. Lab. Clin. Med., in press (1997); Brown, L. F., et al. Amer. J. Pathol. 142:273–283 (1993); Clark, R. A. F., et al. J. Invest. Dermatol. 79:624–629 (1982); Ciano, P. S., et al. Lab. Invest. 54:62–69 (1986); Dejana, E., et al. J. Clin. Invest. 75:11–18 (1985)). Thrombin also has been shown to exert proliferative effect on various cells including fibroblasts, endothelial cells, and to enhance wound healing in rat skin (Kang, Y. H., et al. J. Histochem. Cytochem. 39:413–423 (1991); Shuman, F., NY Acad. Sci. 408:228–235 (1986); Biedermann, B., et al. J. Lab. Clin. Med. 124:339–347 (1994)).

Fibrin microbeads have been described in the prior art for use as drug delivery systems ((Ho, et al. Drug Dev. and Ind. Pharm. 20(4):535–546 (1994); Senderoff, et al. J. Parenteral Sci. & Tech. 45(1):2–6 (1991)). However, it has not been suggested or taught in the prior art that such fibrin microbeads have chemotactic and/or proliferative effects on any cells. Furthermore, the fibrin microbeads of Ho, et al. and Senderoff, et al. would not be particularly useful or desirable as vehicles for culturing cells. In this regard, the Ho, et al. microbeads contain glutaraldehyde which cross-links proteins and destroys certain biologically active sites, thereby interfering with the binding of the microbeads to cells. Glutaraldehyde treatment may also render the microbeads immunogenic. The Senderoff, et al. microbeads contain essentially the same relatively low degree of cross-linking as fibrin. Thus, the Senderoff, et al. microbeads are not stable in aqueous solutions and therefore would not be useful as vehicles for culturing cells which require matrices that do not readily dissolve in aqueous solutions. U.S. Pat. No.

6,150,505 describes novel fibrin microbeads and their method of manufacture, where the fibrin microbeads are provided in the absence of glutaraldehyde.

One problem in the use of these medical or medicinal treatments is the application of the solids, particulates, fluid or otherwise flowable materials to the desired site. Sprinkling a material over the surface of a wound is effective, but can waste significant amounts of materials. It is desirable to be able to apply the materials more uniformly and specifically to a site. U.S. Pat. No. 6,241,697 shows a non-contact wound covering for covering a wound. A peripheral sealing ring is covered by a barrier layer and this assembly is attached to the skin with an adhesive. The barrier layer and peripheral sealing ring together define a treatment volume over the wound. The barrier layer may include active and passive heaters and the sealing ring may dispense water to control the humidity of the treatment volume. One form of active heat is the transfer of a heated fluid to the wound covering. In effect, an enclosed area is defined around a wound and liquid is directed into the enclosed area through a hose or tube.

U.S. Pat. No. 4,373,519 provides a system for removing liquids from a wound to promote healing, and embeds absorbent materials into a non-woven web that is applied to a surface. The non-woven web may be adhesively secured to the wound area.

These and other descriptions in the art provide means to cover or treat wounds, but improvements in the applying and securing of healing materials to wounds would be useful. It is always desirable to find alternative delivery solutions to wound management problems.

SUMMARY OF THE INVENTION

A delivery system is described for the delivery of flowable medicinal, therapeutic or medicine materials. The delivery system comprises a strip having flowable material contained and restrained therein. A removable seal is provided, so that when the removable seal is removed, the flowable material will flow from a storage area onto the site selected for treatment. The removable seal may be provided with additional features such as absorbent coatings, or additional disinfectants coatings useful in preparing the wound surface to receive the flowable wound treatment material. The delivery system may be contained in an adhesively securable element such as a bandage, band-aid, applique', wrap, patch, or the like. The system may be secured to a patient along a limited amount of the edge of the system, the removable seal removed, causing the contained material to flow, and additional edges of the system secured to the patient. The securing of the system may be effected by adhesives, such as activatable adhesives (e.g., solvent or water activated adhesive) or pressure-sensitive adhesive. A preferred composition is a system, article and method for the enhancement of clotting in wounds with extravascular blood flow, especially where the surface of the tissue has been broken. The composition consists of biotolerable, porous particulates (with pores chosen of the appropriate size for the effect desired) applied to the surface of a wound with liquid blood thereon. The porous nature of the particulate material, either free-flowing or packaged or restrained on or in a surface, enhances clotting. Chemical or biochemical agents, such as additional clotting agents, therapeutic agents, antibiotics, clot strengthening agents (such as fibrous structural materials), and the like may optionally be included on, with or within the porous particles. Where the porous particle clotting agents are used with animals, materials which are mildly repellant to the animal patient (without being toxic) may be included within the applied particle material to assure that the animal will not tamper with the wound during healing, a common problem with veterinary treatments. The particles may comprise such diverse materials as organics, metallics, inorganics, ceramics, and the like, both natural and artificial. It is generally preferred that the pore size distribution lies within a general range, and this range may vary from animal to animal and condition to condition, but generally falls within about 0.5–1000 NM or 1 to 1000 nm, or about 5 to 500 nm, depending upon the particular use.

DETAILED DESCRIPTION OF THE INVENTION

A delivery system for applying material to a limited surface area, particularly limited surface areas on the skin of a patient provides a simple, efficient, and focused delivery of flowable material. Flowable material can include liquids, gels, dispersions, emulsions, and most preferably powders or particulates. The system fundamentally works by providing a storage area for the flowable material to be applied and a removable cover over the flowable material. By removing the removable cover, the flowable material is allowed to flow. The system is first contacted with the surface to which the flowable material is to be applied, preferably the system is adhered to the surface along at least one edge, pressure may be applied to the outer surface to hold the flowable material against the wound (or the natural tension of the tape against the wound can provide restraining pressure), the cover is removed, and the flowable material is applied to the surface. The system may optionally then be secured along additional edges to fix the system into place.

The system comprises at least two layers, a top layer and the removable cover layer, the top layer and the cover layer forming a containment zone or pocket holding a predetermined volume of flowable material and restraining the flowable material from flowing outside the pocket. By removing the cover, the flowable material is allowed to flow out of the pocket. Where the system is pressed against a surface and the cover is removed and then the system is pressed against the surface, the pocket is essentially reformed, with the surface replacing the cover, and the flowable material is provided on the site, and will not flow away from the site, but will continue to be available to flow to and into the site to fill a wound or to replace material that is diminished through use or evaporation.

The cover may be removable in a number of fashions. The cover may be a single layer that is peeled from the front (the attached edge) to the back or from the back to the front to expose the flowable material in the pocket. A slide construction may be provided where at least one edge of the cover and preferably both edges of the cover slide along a path or track, so that the entire cover layer can be pulled and withdrawn from over the pocket. Alternatively, a double fold cover (e.g., a single sheet folded over itself) may be placed over the pocket. By pulling one edge of the double fold cover, both sides of the double fold cover are slowly removed from over the pocket. Other mechanical constructions and designs can be used, as long as the cover can be removed to expose the material in the pocket. The cover may be modified by additional structure described herein to provide additional features or functions such as removal of excess blood or exudates before the flowable material is exposed by removing the cover.

The material composition of the elements of the delivery system are basically important only with their ability to function as layers. Materials typically used for tapes, sheets, bandages, band-aids, patches, and the like may be used, as long as they prevent premature or excessive flow of the entrapped flowable material from the pocket or through the composition of the layers. Typical layer materials include fabrics (particularly those with small pores that would prevent flow or loss of the contained material through the pores), filled fabric, polymeric film, natural film, reinforced film, metallized layers, thin metal layers, and combinations of materials. Thermoplastic polymeric film, fabric, and mixtures of polymers and film-forming materials are preferred.

A particularly preferred composition which may be used for the enhancement of the clotting of blood in animals, including mammals, avians and reptiles comprises porous particulate material which is applied to the wound when there is blood in a liquid or only partially clotted state (e.g., where it may wet the particles). The particles may be applied to the wound area either as a free flowing powder of the particles, a dry spray of particles, a moist spray or aerosol of the particles, as an association of particles in or on a carrier (such as a web, tape, fabric, foam, reticulated foam, or film), and may optionally contain conventional clotting agents with the particles. The particle application should enable direct contact of the particles with the flow of blood, preferably without any non-clotting intermediate film or material between the blood at the site of the wound and the clotting particles. For example, the use of the particles on the surface of a film with that surface facing the wound would be acceptable. In that orientation, the blood would clot on the wound site. On the other hand, where a fairly thick, but porous film was used, and the blood flowed through the pores of the film (e.g., greater than 0.1 mm thickness) to reach the porous clotting particles on a backside of the film, the clot would not occur on the wound site. That would not be the most advantageous location for the clot enhancing particles. An intermediate and acceptable structure would be to have the particles located within a thin, light fibrous mass so that as the particles enhanced clotting, the fibers would remain within the region of clotting and strengthen the clot. The fibers could also be used to assist in carrying optional materials (e.g., antibiotics) to the wound site. One type of desirable materials of this last format would have a woven, non-woven or knitted fibrous sheet (e.g., less than 1 mm in thickness, e.g., 0.05 to 0.5 mm, or 0.1 to 0.5 mm thick) with the fabric having a porosity of at least 30% (e.g., 30–95%, 40–95%, or 50–95% porosity), with at least a portion of the porosity filled with the clot enhancing particles described for use in the practice of the present invention. The particles may be carried within the structure of the fabric or bonded to the fibers, filaments, or yarns of the fibrous material (taking care not to completely fill the pores of the particles with any binder used).

The particles may generally have a size of from about 1 to 1000 micrometers, or 1 to 500 micrometers, but the size may be varied by one ordinarily skilled in the art to suit a particular use or type of patient and depending on the ability of a carrier to support the particles with their optional selection of sizes. Examples of specific materials useful in the practice of the present invention comprise porous materials from within the classes of polysaccharides, cellulosics, polymers (natural and synthetic), inorganic oxides, ceramics, zeolites, glasses, metals, and composites. Preferred materials are of course non-toxic and are provided as a sterile supply. The polysaccharides are preferred because of their ready availability and modest cost. The porous particulate polysaccharides may be provided as starch, cellulose and/or pectins, and even chitin may be used (animal sourced from shrimp, crab and lobster, for example). Glycosaccharides or glycoconjugates which are described as associations of the saccharides with either proteins (forming glycoproteins, especially glycolectins) or with a lipid (glycolipid) are also useful. These glycoconjugates appear as oligomeric glycoproteins in cellular membranes. In any event, all of the useful materials must be porous enough to allow blood liquid and low molecular weight blood components to be adsorbed onto the surface and/or absorbed into the surface of the particles. Porosity through the entire particle is often more easily achieved rather than merely etching the surface or roughening the surface of the particles.

Ceramic materials may be provided from the sintering, or sol-gel condensation or dehydration of colloidal dispersions of inorganic oxides such as silica, titanium dioxide, zirconium oxide, zinc oxide, tin oxide, iron oxide, cesium oxide, aluminum oxide and oxides of other metal, alkaline earth, transition, or semimetallic chemical elements, and mixtures thereof. By selection of the initial dispersion size or sol size of the inorganic oxide particles, the rate of dehydration, the temperature at which the dehydration occurs, the shear rate within the composition, and the duration of the dehydration, the porosity of the particles and their size can be readily controlled according the skill of the ordinary artisan.

With regard to cellulosic particles, the natural celluloses or synthetic celluloses (including cellulose acetate, cellulose butyrate, cellulose propionate, etc.) may be exploded or expanded according to techniques described in U.S. Pat. No. 5,817,381 and other cellulose composition treating methods described therein which can provide porous particles, fibers and microfibers of cellulose based materials. Where the porous materials, whether of cellulose or other compositions, have a size which may be too large for a particular application, the particles may be ground or milled to an appropriate size. This can be done by direct mortar and pestle milling, ball milling, crushing (as long as the forces do not compress out all of the porosity), fluidized bed deaggregation and size reduction, and any other available physical process. Where the size of the raw material should be larger than the particle size provided, the smaller particles may be aggregated or bound together under controlled shear conditions with a binder or adhesive until the average particle size is within the desired range.

Porosity may be added to many materials by known manufacturing techniques, such as 1) codispersion with a differentially soluble material, and subsequent dissolution of the more soluble material, 2) particle formation from an emulsion or dispersion, with the liquid component being evaporated or otherwise removed from the solid particle after formation, 3) sintering of particles so as to leave porosity between the sintered or fused particles, 4) binding particles with a slowly soluble binder and partially removing a controlled amount of the binder, 5) providing particles with a two component, two phase system where one component is more readily removed than another solid component (as by thermal degradation, solubilization, decomposition, chemical reaction such as, chemical oxidation, aerial oxidation, chemical decomposition, etc.), and other known process for generating porosity from different or specific types of compositions and materials. Where only surface porosity is needed in a particular clot promoting format, surface etching or abrasion may be sufficient to provide the desired surface porosity.

A particularly desirable and commercially available material comprises polysaccharide beads, such as dextran beads which are available as Sephadex™ beads from Pharmacia Labs. These are normally used in surgery as an aid to debridement of surfaces to help in the removal of damaged tissue and scar tissue from closed wounds. The application of this type of porous bead (and the other types of porous beads, such as those formed from crosslinked starch) to open wounds with blood thereon has been found to promote hemostasis, speeding up the formation of clots, and reducing blood loss and the need for continuous cleaning of the wound area. Bleeding from arteries, veins and small capillaries, soft tissue, organs (e.g., liver, kidney, lungs and spleen) can be effectively managed, reduced and eliminated in most cases by application of the particles or beads according to the present invention.

The porous particles or porous beads may be directly applied to surfaces or held in place by pressure. The beads or particles may be free flowing or be supported on or in a containment system. For example, the particles may be adhered to the surface of a sheet or film which is applied (e.g., contacted, wrapped, adhered, secured, affixed or otherwise place into a position where blood on the wound area will be absorbed or adsorbed by the porous particles or porous beads) to areas of a wound with blood thereon. The particles may also be provided in a form where the porous particles or porous beads may be interspersed with fibers, filaments or other particles in a self-supporting structure, entangled within the fibrous elements of a net, web, fabric or sheet, embedded in a sheet or film (with the particles exposed to enable adsorption or absorption of blood in contact with the wound), a packet of material, with the particles or beads free-flowing within the confines of the packet. The terms particles and beads are not intended to denote any substantive difference in size, shape or performance of materials and are not asserted as having any distinct differences within the practice of the present invention, but are merely alternative terms. The use of only one term does not intend that the other term is not equally applicable in the context in which the one term is used. The porous particles and porous beads may also be provided as part of a patch system, with a fibrous network associated with the particles to provide a high level of structural integrity and strength to the applied assembly over the wound, even before clotting has occurred. This would be particularly appropriate where the assembly was being used as a stitch replacement or true wound closure system rather than only promoting clotting.

The porous particles may easily be associated with or carry additional, but optional, clotting or wound treating materials or ingredients. For example, it would be desirable to provide the porous particles with antibiotics, antifungal agents (especially where application may be in a tropical environment), topical pain reducing medication, pharmaceuticals, anti-inflammatants, tissue enzyme inhibitors (e.g., epsilon aminocaproic acid, to reduce tissue enzyme production that would weaken the blood clot), and the like. Existing materials which promote clotting or control bleeding would be particularly, such as thrombin, fibrinogen, aprotinin, fibronectin, and factor XIII. However, one of the advantages of the materials which may be used (excluding those derived from animals) is that they are not made from animal components as are the typical clotting or wound treatment materials noted above. As there is always a potential for animal based materials being a source of infection themselves (e.g., viral infection, spongiform encephalopathy, allergic reactions, etc.), the avoidance of animal based products, which can be easily accomplished in the practice of the present invention, is desirable.

The preferred polysaccharide components for the porous particles and porous beads of the present invention may often be made from cross-linked polysaccharides, such as cross-linked dextran (poly[beta-1,6-anhydroglucose]) or starch (poly{alpha-1,4-anhydroglucose]). Dextran is a high molecular weight water-soluble polysaccharide. It is not metabolized by humans, is non-toxic, and is well tolerated by tissue in most animals, including most humans. There has even been extensive use of solubilized dextrans as plasma substitutes. Similarly, beads prepared by cross linking starch with epichlorohydrin are useful as hemostatic agents and are well tolerated by tissue. The starch particles are enzymatically degraded by tissue alpha-amylases and rapidly removed from the wound site. The Sephadexm™ beads specifically mentioned in the description of particularly useful polysaccharides comprise dextran crosslinked with epichlorihydrin. These beads arc available in a variety of bead sizes (e.g., 10 to 100 micrometers, with a range of pore size. It is believed that pore sizes on the order of from 5 to 75% of volume may be commercially available and can be expanded to from 5 to 85% by volume or manufactured with those properties from amongst the type of beads described above. The sizes of the pores may also be controlled to act as molecular sieves, the pore size being from 0.5% or 1 to 15% of the largest diameter of the particles or beads. The Sephadex™ beads are promoted as having controlled pore sizes for molecular weight cutoff of molecules during use as a sieve, e.g., with cutoff molecular being provided at different intervals between about 5,000 Daltons and 200,000 Daltons. For example, there are cutoff values specifically for molecular weight sizes of greater than 75,000 Daltons. This implies a particle size of specifically about 10 to 40 microns. These beads will rapidly absorb water, swelling to several times their original diameter and volume (e.g., from 5 to as much as twenty times their volume). Similar technology can be used to produce cross linked starch beads with properties similar to the Sephadex™ particles. Other soluble polysaccharides such as sodium alginate or chitosan can be used to prepare cross linked beads with controlled porosity and size.

Major classes of pressure-sensitive adhesives include tackified natural rubbers; synthetic rubbers such as butyl rubber; and tackified linear, radial, star, and branched and tapered styrene block copolymers, such as styrene-butadiene, styrene-ethylene/butylene and styrene-isoprene; polyurethanes; polyvinyl ethers; acrylics, especially those having long chain alkyl groups; poly-α-olefins; and silicones.

Generally, when additives are used to alter properties of pressure-sensitive adhesives, the additives need to be miscible with the pressure-sensitive adhesive or to form homogeneous blends at the molecular level. Some types of pressure-sensitive adhesives have been modified with tackified thermoplastic elastomers, thermoplastics, and elastomers. For example, thermoplastic materials have been added to polymerized hot melt acrylic pressure-sensitive adhesives wherein the thermoplastic is a packaging material or recyclable tape backings. In these cases, the type and amount of thermoplastic material is controlled so that the thermoplastic material can function as a packaging material while avoiding degradation of the adhesive properties of the pressure-sensitive adhesive.

However, more often than not when a non-tacky thermoplastic additive is blended with a pressure-sensitive adhesive, reduction of the overall adhesive properties of the blend (as compared to the pressure-sensitive adhesive only) are observed. Thermoplastic polymers have been added to styrene block copolymer adhesives to reduce the tack of the resulting pressure-sensitive adhesives for application of protective sheets to large area surfaces.

Pressure-sensitive adhesives, whether modified or not have been used for more than half a century for a variety of purposes. Generally, pressure-sensitive adhesives are used in tapes wherein a tape comprises a backing, or substrate, and a pressure-sensitive adhesive. Typically, a pressure-sensitive adhesive adheres with no more than applied finger pressure and can be permanently tacky.

In the medical field, pressure-sensitive adhesive tapes are used for many different applications in the hospital and health areas. For most applications, tapes are applied directly to a patient's skin. It is important that the pressure-sensitive adhesive tape be compliant and non-irritating to the skin, as well as adhering to the skin without causing damage to the skin when the tape or adhesive coated article is removed. A particularly useful medical application for pressure-sensitive adhesive tapes and articles is in the field of transdermal patches. Such patches can be used as drug transport membranes or to attach drug transport membranes to skin.

Although pressure-sensitive adhesive tapes and articles are widely used in the medical field, pressure-sensitive adhesive tapes and articles find widespread use in many other applications. For example, transfer tapes can be used to adhere two surfaces together such as the flaps of packing material or fabric to a surface. However, transfer tape adhesives generally have little tensile strength and one solution has been to add glass fibers to provide tensile strength.

Pressure-sensitive adhesives require a delicate balance of viscous and elastic properties that result in a four-fold balance of adhesion, cohesion, stretchiness and elasticity. Pressure-sensitive adhesives generally comprise elastomers that are either inherently tacky, or elastomers or thermoplastic elastomers that are tackified with the addition of tackifying resins.

These and other aspects of the invention will be further understood by reference to the figures.

Figure 1:
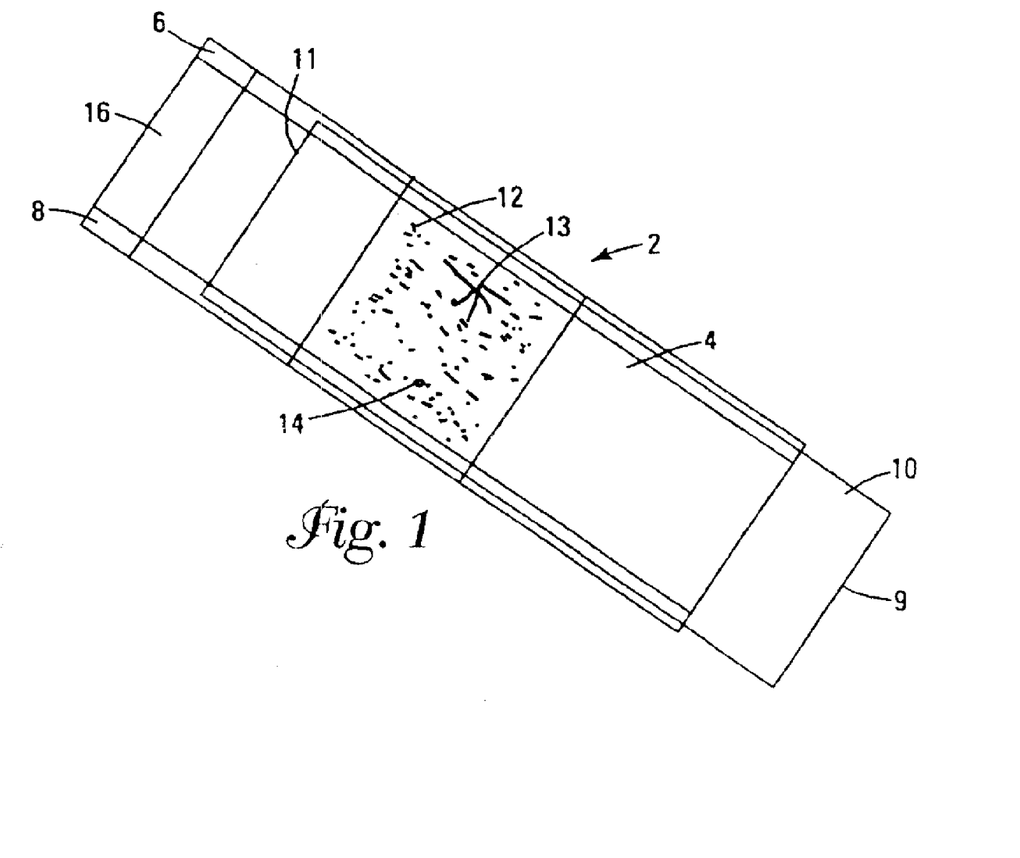
FIG. 1 shows a top perspective view of a slide delivery system of the invention.

FIG. 1 shows a top perspective view of what is referred to as a slidable system device 2. This device 2 has a top sheet 4 that has edges rolled over to form tracks 6 and 8. These tracks 6 and 8 are used to control, guide, and align cover film 10. A pocket area 14 is formed by the top sheet 4 and the cover film 10. The flowable material 13 is shown as particulate material, fills the pocket 14 and is restrained from moving out of the pocket 14 by the top sheet 4 and the cover 10. A pressure-sensitive adhesive area 16 is provided on the contact side or bottom side of the top sheet 4. In one method of use, the adhesive strip 16 is pressed against a surface (e.g., skin adjacent a wound) to secure the system 2 to the patient, a leading edge 9 of the cover 10 is grasped and pulled, sliding the cover 10 along the tracks 6 and 8, removing the cover 10 as the trailing edge 11 of the cover passes over the pocket 14, and allows the flowable particulate material 13 to flow from the pocket 14 onto the surface of the patient (not shown). By keeping the top sheet 4 relatively close to the surface, flow of the material 13 away from the targeted site can be controlled. By having pressure-sensitive adhesive along the outermost surface of the tracks 6 and 8, the system 2 can be further adhered to the surface to limit flow of material 13 away from the site. This is further shown and explained in FIG. 2.

Figure 2:
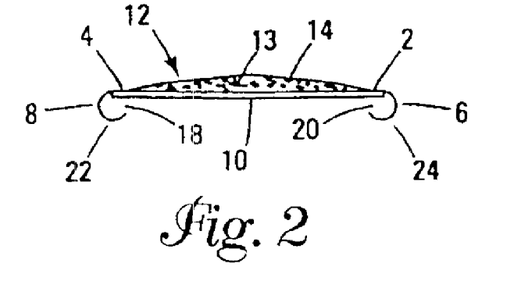
FIG. 2 shows an end view of the slide delivery system of the invention.

FIG. 2 is an edge view of a slidable delivery system as in FIG. 1. The top sheet 4 is shown with the rolled edges 6 and 8 more clearly displayed. The cover 10 is shown to be within the rolled edges 6 and 8, which provide tracks 18 and 20 for the cover 10, forming the pocket 14 to enclose the flowable particulate material 13 under the bubble 12 formed by the top sheet 4. The bottom faces 22 and 24 of the rolled edges 6 and 8 may have adhesive (e.g., solvent activatable adhesive or pressure-sensitive adhesive) to assist in the final fixing or securing of the system 2 to a surface, especially after removal of the cover 10. In this system, the adhesive securement on faces 22 and 24 may be made before sliding the cover 10 out of the system 2 and allowing the material 13 to flow, as the faces 22 and 24 do not interfere with movement of the cover 10.

Figure 3:
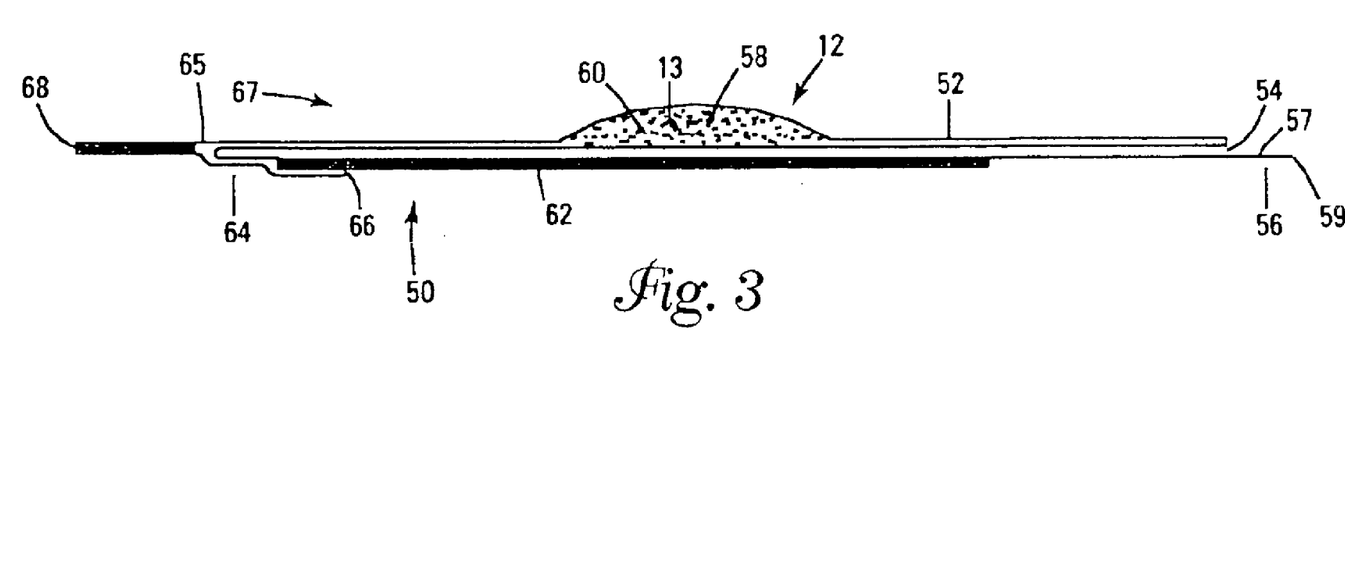
FIG. 3 shows a side view of a stripping delivery system of the invention.

FIG. 3 is another embodiment of a delivery system 50. The top sheet 52 again forms a bubble 12 that forms an enclosing area 60 that entraps flowable material 13. The flowable material is trapped between the top sheet 52 and the top fold 54 of the folded cover sheet 57. By pulling on the end 59 of the lower 56 (or in reverse the upper 54) half of the folded cover sheet 57, the cover sheet 57 is removed, exposing the entrapped flowable material, here shown as particulates 58. By pulling on the edge 59, the trailing fold edge 65 is pulled in a direction 67 that will uncover the entrapped flowable material 13. Also shown in FIG. 3 is an absorbent layer 62 on the exposed surface of the bottom fold layer 56. As the bottom fold layer 56 is withdrawn by pulling the edge 59, the absorbent material 62 wipes the surface. Where there is blood, grit or dirt on the surface, the absorbent layer can assist in removing those before the particulate flowable material 13 is deposited on the site. The absorbent layer may also contain disinfectant or antibiotics to pre-treat a wound area. An edge coating of pressure-sensitive adhesive 68 is shown, with a strippable cover sheet 64 having a release surface 66.

Figure 4:
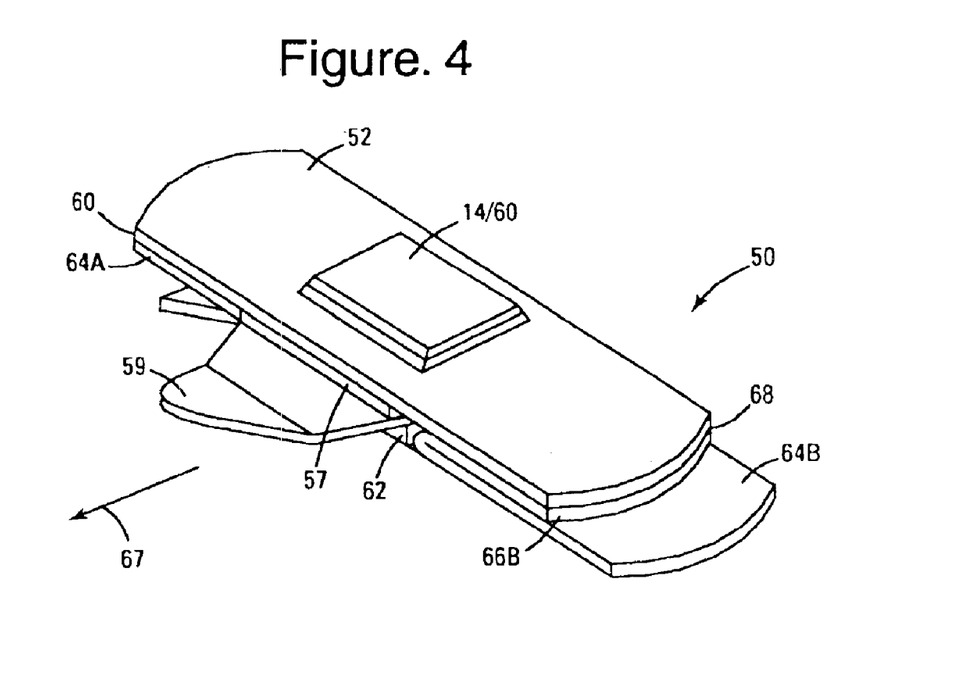
FIG. 4 shows a perspective view of a delivery system according to the invention with a side release pull strip.

FIG. 4 shows an alternative construction for a delivery system 50. The top sheet 52 again forms a containment area 14 that forms an enclosing area 60 that entraps flowable material Not shown). The flowable material is trapped between the top sheet 52 and a withdrawable stem/cover 59 attached to a lower shield/cover 57 blocking release of the flowable material until the shield/cover 57 is removed. By pulling on the stem/cover 59, the lower shield cover 57 is removed, allowing the flowable material to flow. Three separate strippable elements 62, 64A, and 64B are shown. The strippable elements may be removed at various times, with the following sequence being merely exemplary. Strippable cover 62 is removed to ease the removability of the cover/shield 57 (or this layer 62 may be left on the delivery system). One or both of the end strippable cover sheets 64A and 64B are removed (eventually both should be removed) to expose pressure-sensitive adhesive end tabs 66A and 66B to assist in securing the delivery system 50 to a patient's wound area. After the delivery system 50 is attached to a patient, the tab 59 is pulled in direction 67, removing the cover 57 and allowing the contained flowable material (not shown) to flow towards the intended area.

Figure 5:
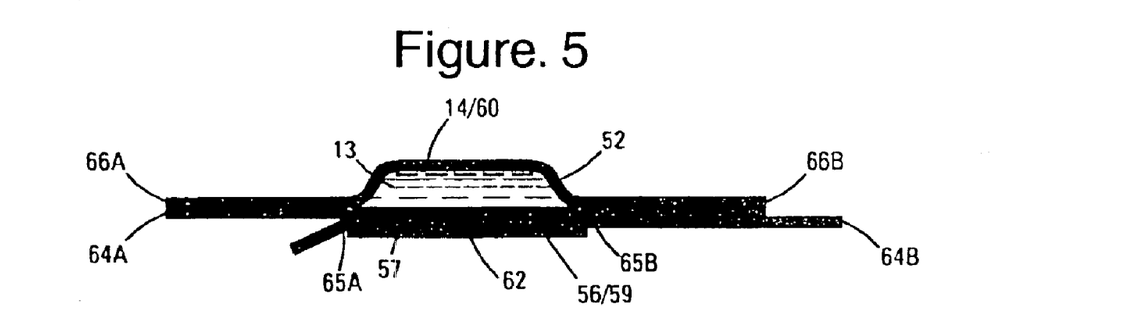
FIG. 5 shows a side view of the delivery system of FIG. 4 with a side release pull strip.

FIG. 5 shows a side view of the delivery system 50 of FIG. 4. In FIG. 5, the entrapped flowable material 13 is shown, as are the other elements of FIG. 4. As shown in this Figure, the strippable elements 64A and 64B are shown as folded elements with upper half of the folds 65B and 65A in contact with the pressure-sensitive adhesive tab ends 66B and 66A, respectively.

These examples are intended to be instructive rather than limiting in interpreting the scope of the invention. Other variations and materials will be apparent to those of ordinary skill in the art, particularly with regard to the selection of structural and functional materials in the delivery system of the invention.

What is claimed is:

1. A delivery system for use in the delivery of materials to a surface, the delivery system comprising:
   a top layer restraining movement of a flowable material;
   one or more cover layers restraining movement of the flowable material;
   a pocket formed between the top layer and the cover layer that restrains a
   flowable material between the top layer and the cover layer;
   flowable material in the pocket;
   an adhesive along at least one edge or end of the delivery system so that the delivery system can be adhered to a surface, and the cover then removed from the delivery system while the adhesive adheres the delivery system to the surface, thereby allowing the flowable material to be able to flow from the pocket.

2. The delivery system of claim 1 wherein the flowable material comprises a particulate material.

3. The material delivery system of claim 2 wherein the particulate material comprises porous particulate material having an average particle diameter of from about 1 to 1000 micrometers.

4. The material delivery system of claim 3 wherein the porous particulate material has an antibiotic carried on the particles.

5. The material delivery system of claim 3 wherein the porous particles have molecular sieve cutoff values between about 5,000 Daltons and 200,000 Daltons.

6. The material delivery system of claim 3 wherein pores comprise from 5 to 75% by volume of the porous particles.

7. The material delivery system of claim 3 wherein the porous particles comprise dextran.

8. The material delivery system of claim 7 wherein the dextran is crosslinked.

9. The material delivery system of claim 2 wherein the cover can be linearly pulled and slid from under the pocket.

10. The material delivery system of claim 2 wherein the cover comprises two layers attached to each other at only one end of the cover.

11. The material delivery system of claim 1 wherein the top layer has a top side and a bottom side, and the top layer has a first edge and an opposite second edge, and at least the first edge has an adhesive on the bottom side.

12. The material delivery system of claim 11 wherein the adhesive comprises a pressure-sensitive adhesive.

13. The material delivery system of claim 12 wherein there is a strippable cover layer over the pressure-sensitive adhesive.

14. The material delivery system of claim 13 wherein the cover can be linearly pulled and slid from under the pocket.

15. The material delivery system of claim 12 wherein the cover can be linearly pulled and slid from under the pocket.

16. The material delivery system of claim 12 wherein the cover comprises two layers attached to each other at only one end of the cover.

17. The material delivery system of claim 16 wherein a bottom layer of the two layers of the cover has an absorbent material on its exposed face.

18. The material delivery system of claim 11 wherein the cover can be linearly pulled and slid from under the pocket.

19. A method of applying flowable material to a surface comprising providing a system comprising a top layer and a cover layer, the top layer and cover layer forming a pocket entrapping a flowable material, securing at least one edge to the surface subsequently, removing the cover layer, and allowing the flowable material to flow onto the surface.

20. The method of claim 19 wherein the flowable material comprises a solid particulate material.

21. The method of claim 20 wherein the surface comprises skin including a wound.

22. The method of claim 21 wherein the solid particulate comprises a dextran.

23. The method of claim 19 wherein securing at least one edge to the surface is effected by an adhesive.

24. The method of claim 21 wherein securing at least one edge to the surface is effected by an adhesive.

25. The method of claim 24 wherein the adhesive comprises a pressure-sensitive adhesive.

26. The method of claim 24 wherein after removing the cover layer, an edge other than the at least one edge is also secured to the surface.

27. A method for treating a surface of an organism having a wound therein comprising:
   adhering the adhesive along at least one edge of the delivery system of claim 1 so that the delivery system is adhered to the surface of an organism,
   removing the cover from the delivery system while the adhesive adheres the delivery system to the surface, thereby allowing the flowable material to be able to flow from the pocket.

28. The method of claim 27 wherein pressure is applied to the system prior to removing the cover.

29. A delivery system for use in the delivery of materials to a surface, the delivery system comprising:
   a top layer restraining movement of a solid particulate flowable material;
   one or more cover layers restraining movement of the solid particulate flowable material;
   a pocket formed between the top layer and the cover layer that restrains a solid particulate flowable material between the top layer and the cover layer;
   solid particulate flowable material in the pocket; an adhesive along at least one edge or end of the delivery system so that the delivery system can be adhered to a surface, and the cover then removed from the delivery system while the adhesive adheres the delivery system to the surface, thereby allowing the solid particulate flowable material to be able to flow from the pocket.

* * * * *